United States Patent [19]
Musser et al.

[11] Patent Number: 4,942,236
[45] Date of Patent: Jul. 17, 1990

[54] 2-ARYL SUBSTITUTED PYRIDYL-CONTAINING PHENYL SULFONAMIDO COMPOUNDS AS ANTIALLERGIC AND ANTIINFLAMMATORY AGENTS

[75] Inventors: John H. Musser, Malvern; Reinhold H. W. Bender, Valley Forge; Anthony F. Kreft, III, Trooper, all of Pa.

[73] Assignee: American Home Products Corporation, New York, N.Y.

[21] Appl. No.: 311,558

[22] Filed: Feb. 15, 1989

Related U.S. Application Data

[62] Division of Ser. No. 103,224, Sep. 30, 1987, Pat. No. 4,826,990.

[51] Int. Cl.$^5$ .................. C07D 213/76; C07D 213/42
[52] U.S. Cl. .................... 546/334; 546/276; 546/277; 546/330; 546/337
[58] Field of Search ................. 546/337, 334

[56] References Cited

U.S. PATENT DOCUMENTS 4,355,034 10/1982 Shen et al. .................... 514/252

Primary Examiner—Alan L. Rotman
Attorney, Agent, or Firm—George Tarnowski

[57] ABSTRACT

There are disclosed compounds of the formula

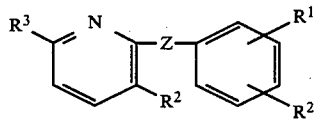

wherein

-continued

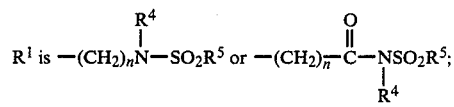

Z is $-(CH_2)_nO-$, $-(CH_2)_nS-$, $-(CH_2)_n\overset{O}{\underset{\|}{S}}-$ or $-(CH_2)_nSO_2-$;

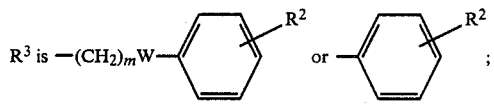

$R^1$ is $-(CH_2)_n\overset{R^4}{\underset{|}{N}}-SO_2R^5$ or $-(CH_2)_{\overline{n}}\overset{O}{\underset{\|}{C}}-\overset{}{\underset{R^4}{N}}SO_2R^5$;

n is 0–5;
$R^2$ is, independently, hydrogen, loweralkyl, loweralkoxy, trifluoromethyl or halo;

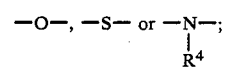

$R^3$ is $-(CH_2)_mW-$ ... or ... ;

W represents a bond or $-O-$, $-S-$ or $-\overset{}{\underset{R^4}{N}}-$;

m is 1–15;
$R^4$ is hydrogen or loweralkyl;
$R^5$ is lower alkyl, monofluoroloweralkyl, difluoroloweralkyl, polyfluoroloweralkyl, perfluoroloweralkyl or

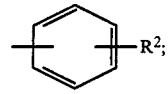

or a pharmaceutically acceptable salt thereof, and their use in the treatment of leukotriene-mediated naso-bronchial obstructive airpassageway conditions, such as allergic rhinitis, allergic bronchial asthma and the like, and as antiinflammatory agents.

2 Claims, No Drawings

2-ARYL SUBSTITUTED PYRIDYL-CONTAINING PHENYL SULFONAMIDO COMPOUNDS AS ANTIALLERGIC AND ANTIINFLAMMATORY AGENTS

This invention relates to novel 2-aryl substituted heterocyclic compounds possessing lipoxygenase inhibitory and leukotriene antagonist activity, which are useful as anti-inflammatory and antiallergic agents.

It is known that arachidonic acid (AA) is metabolized in mammals by two distinct pathways. The metabolism of arachidonic acid by cyclooxygenase enzymes results in the production of prostaglandins and thromboxanes. The physiological activity of the prostaglandins has already been amply elucidated in recent years. The other pathway of AA metabolism involves lipoxygenase enzymes and results in the production of a number of oxidative products called leukotrienes. The latter are designated by the LT nomenclature system, and the most significant products of the lipoxygenase metabolic pathway are the leukotrienes $B_4$, $C_4$, $D_4$ and $E_4$. The substance denominated slow-reacting substance of anaphylaxis (SRS-A) has been shown to consist of a mixture of sulfidopeptide leukotrienes, $C_4$, $D_4$ and $E_4$ [see Bach et al., *J. Immun.* 215, 115–118 (1980); *Biochem. Biophys. Res. Commun.* 93, 1121–1126 (1980)].

The significance of these leukotrienes is that a great deal of evidence has been accumulated showing that leukotrienes participate in inflammatory reactions, exhibit chemotactic activities, stimulate lysosomal enzyme release and act as important factors in the immediate hypersensitivity reaction. It has been shown that $LTC_4$ and $LTD_4$ are potent bronchoconstrictors of the human bronchi [see Dahlen et al., *Nature* 288, 484–486 (1980) and Piper, *Int. Arch. Appl. Immunol.*, 76, suppl. 1, 43 (1985)] which stimulate the release of mucus from airways in vitro [Marom et al., *Am. Rev. Resp. Dis.*, 126, 449 (1982)], are potent vasodilators in skin [see Bisgaard et al., *Prostaglandins*, 23, 797 (1982)], and produce a wheal and flare response [Camp et al., *Br. J. Pharmacol.*, 80, 497 (1983)]. The nonpeptide leukotriene, $LTB_4$, is a powerful chemotactic factor for leukocytes [see A. W. Ford-Hutchinson, *J. Roy. Soc. Med.*, 74, 831–833 (1981)], which stimulates cell accumulation and affects vascular smooth muscle [see Bray, *Br. Med. Bull.*, 39, 249 (1983)]. The activity of leukotrienes and mediators of inflammation and hypersensitivity is extensively reviewed in Bailey and Casey, *Ann. Reports Med. Chem.*, 17, 203–217 (1982) and in Bray, *Agents and Actions*, 19, 87 (1986).

Accordingly, the biological activity of the leukotrienes and SRS's, and of lipoxygenase as the enzyme leading to the metabolism of AA to leukotrienes, indicates that a rational approach to drug therapy to prevent, remove or ameliorate the symptoms of allergies, anaphylaxis, asthma and inflammation must focus on either blocking the release of mediators of these conditions or antagonizing their effects. Thus, compounds which inhibit the biological effects of the leukotrienes and SRS's and/or which control the biosynthesis of these substances, as by inhibiting lipoxygenase, are considered to be of value in treating such conditions as allergic bronchial asthma, allergic rhinitis, as well as in other immediate hypersensitivity reactions.

The invention provides novel compounds of the formula

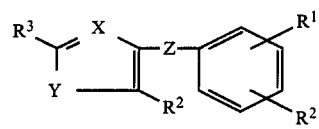

wherein

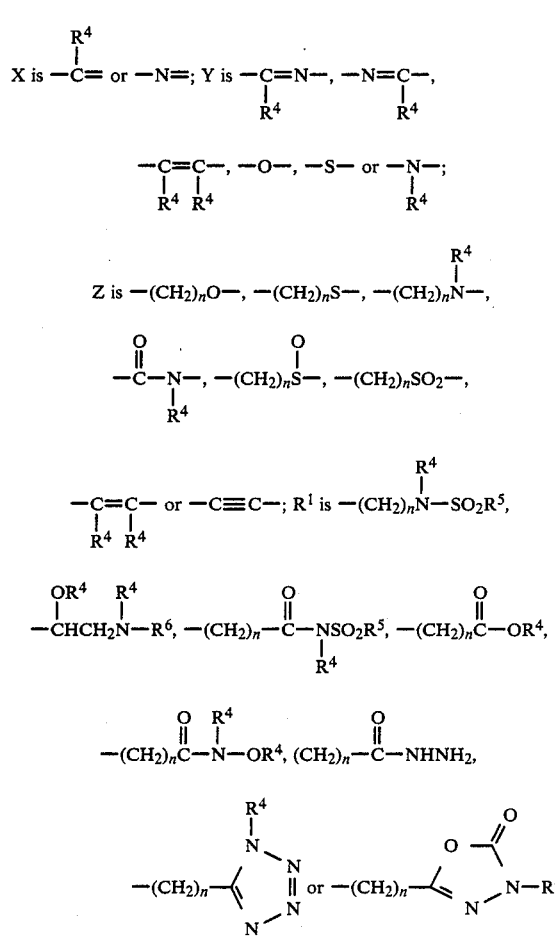

n is 0–5;
$R^2$ is hydrogen, loweralkyl, loweralkoxy, lower alkoxycarbonyl, trifluoromethyl, nitro, cyano or halo;

W represents a bond or

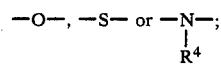

m is 1–15;
$R^4$ is hydrogen or loweralkyl;
$R^5$ is lower alkyl, monofluoroloweralkyl, difluoroloweralkyl, polyfluoroloweralkyl, perfluoroloweralkyl or

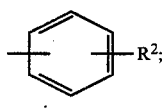

$R^6$ is hydrogen, lower alkyl,

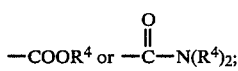

and the pharmaceutically acceptable salts thereof.

The term "halo" refers to fluoro, chloro, and bromo. The terms "loweralkyl" and "loweralkoxy" refer to moieties having 1–6 carbon atoms in the carbon chain.

The compounds of the invention can be prepared via variants of a basic reaction scheme using appropriate starting materials. Thus, compounds in which $R^1$ is the moiety

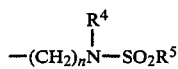

can be prepared by the reaction of an appropriate aniline derivative with an appropriate alkyl sulfonyl chloride or alkyl sulfonic anhydride as follows:

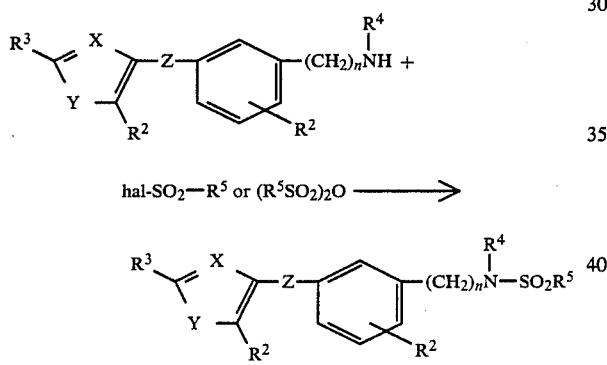

where X, Y, $R^2$, $R^4$, $R^5$ and n are as defined hereinbefore and hal refers to a halo radical, for example, chloro or bromo. The reaction is carried out in an organic solvent, for instance tetrahydrofuran, and at room temperatures. The starting aniline derivatives employed in this reaction sequence and in which, for example Z is —CH₂O—, can be prepared as follows:

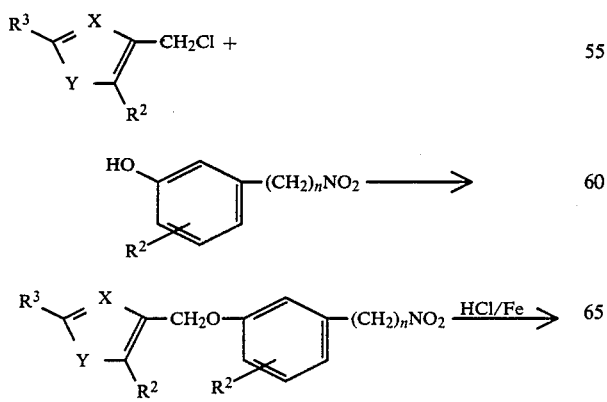

-continued

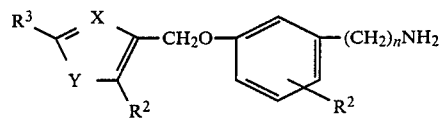

Additionally, those compounds in which $R^1$ is the moiety

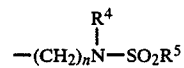

and $R^3$ is lower alkyl, can be readily prepared from the compounds wherein $R^4$ is lower alkyl by the following reaction sequence:

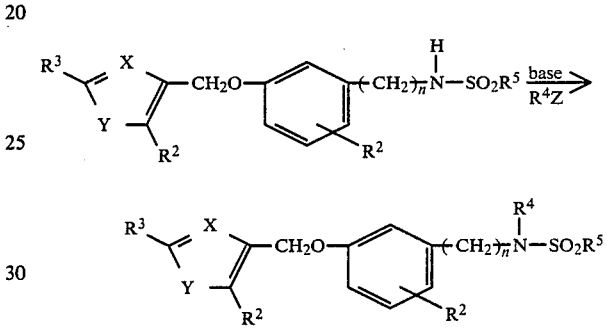

wherein X, Y, $R^2$, $R^4$, $R^5$ and n are as defined hereinbefore and Z is the replaceable portion of the alkylating agent $R^4Z$, which can be any of the conventional alkylating agents, such as for example the alkyl halides, alkyl sulfates, alkyl sulfonates and so forth.

Compounds of the invention in which $R^1$ is

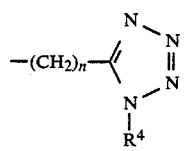

and $R^4$ is hydrogen, can be prepared by the following reaction scheme, where Z is again —CH₂O—:

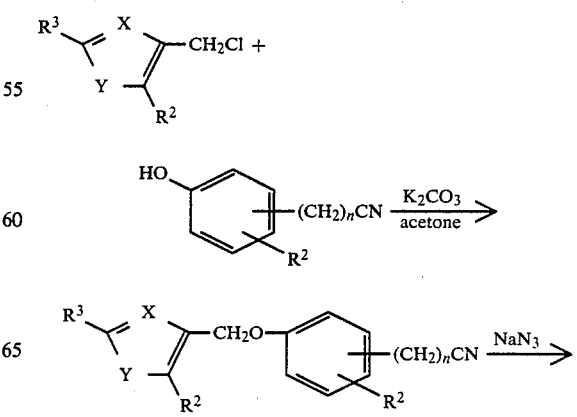

-continued

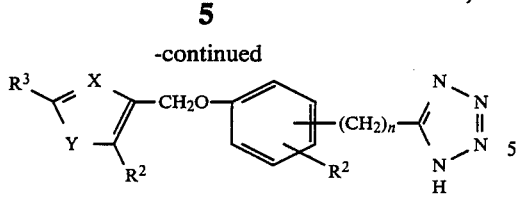

Those compounds in which $R^4$ is lower alkyl can be prepared by alkylating the tetrazole moiety using conventional alkylating agents, such as alkyl halides, alkyl sulfates, alkyl sulfonates and so forth.

Compounds of the invention in which $R^1$ is

can be prepared by the reaction of an appropriate R—, S— or racemic phenylephrine; R—, S— or racemic norphenylephrine; R—, S— or racemic N-ethylphenylephrine; or R—, S— or racemic N-ethylnorphenylephrine derivative with an appropriate benzofused heterocyclic derivative as follows:

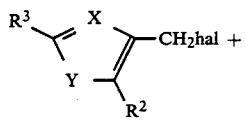

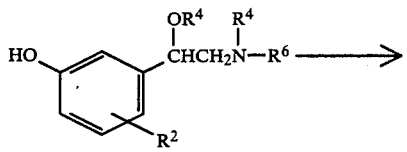

-continued

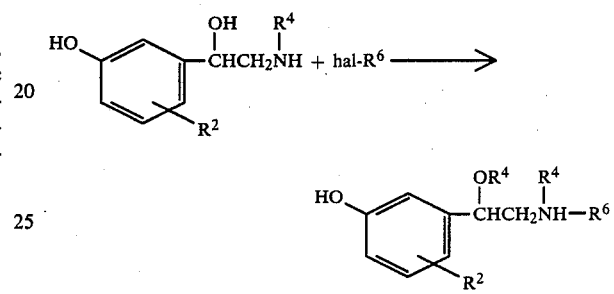

wherein X, Y, $R^2$, $R^4$ and $R^6$ are as defined hereinbefore and hal refers to a halo radical, for example, chloro or bromo. The reaction is carried out in the presence of cesium carbonate in an organic solvent, for instance acetone, under reflux conditions. The various starting phenylephrine-based derivatives employed in the reaction sequence can be prepared as follows (illustrating preparation of a phenylephrine starting material):

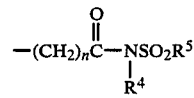

Compounds of the invention in which $R^1$ is $$-(CH_2)_n\overset{O}{\underset{R^4}{\overset{\|}{C}}}-NSO_2R^5$$

or —$(CH_2)_n COOR^4$ can be prepared according to two preparative schemes. For these compounds in which n>2, the following representative sequence is employed:

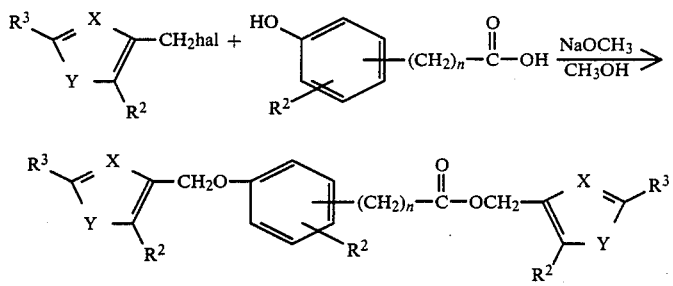

The resulting compounds obtained by this sequence are hydrolyzed to yield intermediate carboxylic acids:

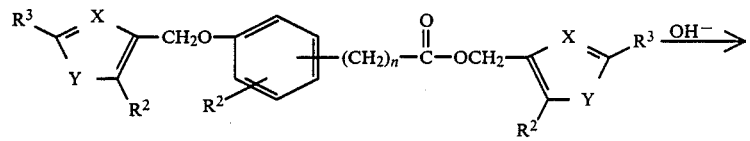

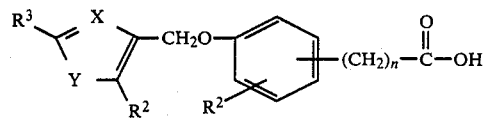

which are then reacted with an appropriate sulfonamide reactant to yield the desired sulfonylcarboxamide derivatives:

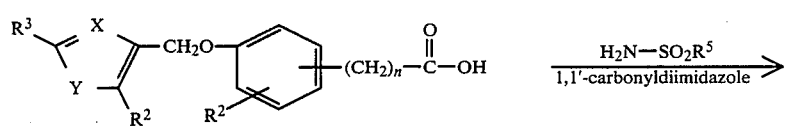

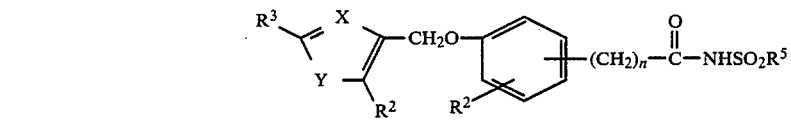

or the carboxylic acid can be esterified to yield the appropriate ester:

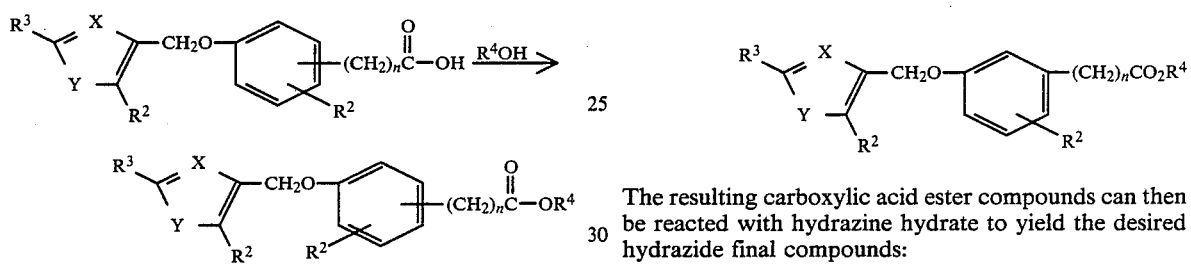

For those compounds in which $R^1$ is

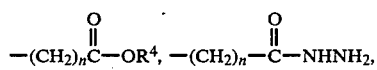

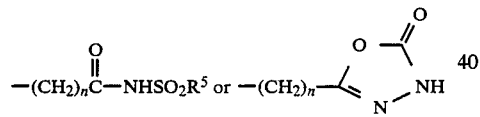

and n is 0 or 1, the following reaction sequence is employed, in which $R^4$ is lower alkyl:

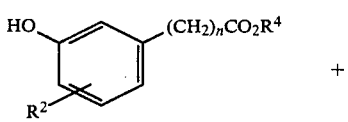

+

-continued

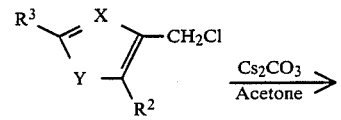

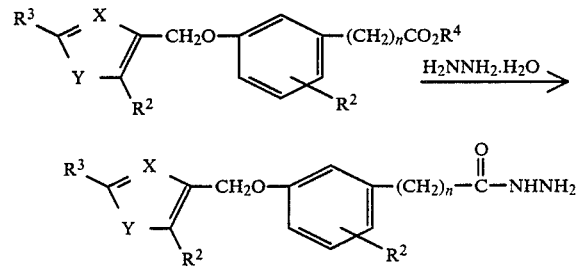

The resulting carboxylic acid ester compounds can then be reacted with hydrazine hydrate to yield the desired hydrazide final compounds:

The latter can be further reacted in the presence of 1,1'-carbonyldiimidazole to yield the final compounds containing the oxadiazolone grouping:

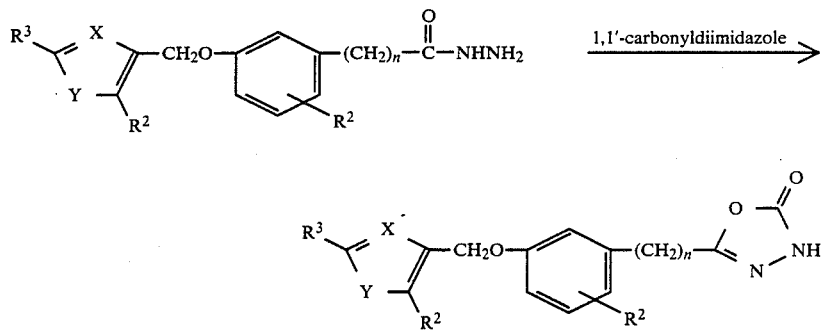

Alternatively, the carboxylic acid ester compounds can be hydrolyzed to the carboxylic acids, which can be then be reacted with the appropriate sulfonamide reactants in order to obtain the desired sulfonylcarboxamide derivatives:

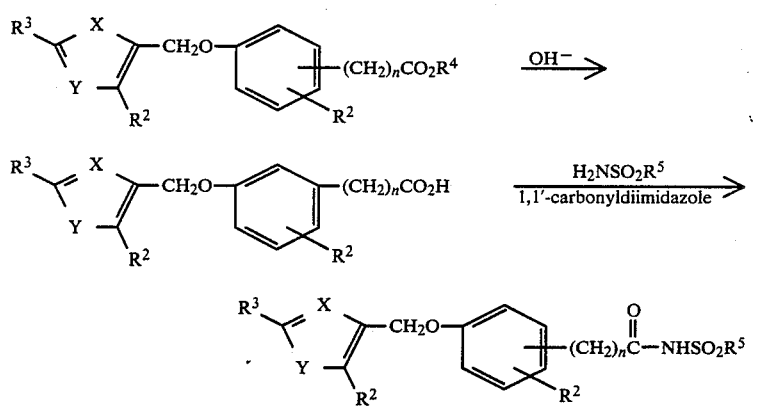

Finally, compounds of the invention in which $R^1$ is

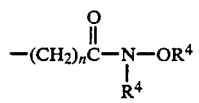

can be prepared using the carboxylic acid ester compounds described in the immediately preceding reaction sequences as starting compounds:

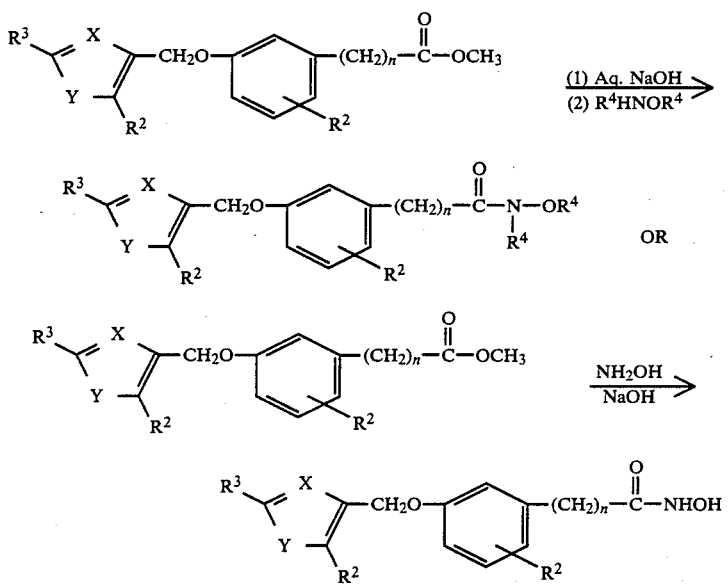

The 2-aryl substituted heterocyclic compounds used as starting material in all the above reaction sequences are either commercially available or can be prepared by methods conventional in the art. Thus, for example, such compounds as 4-(chloromethyl)-5-methyl-2-[4-(methoxy)phenyl] oxazole can be prepared according to the method described by Goto et al., *Chem. Pharm. Bull.*, 19, 2050 (1971); 2-phenyl-4-chloromethylthiazole by the method described by Marzoni, *J. Heterocyclic Chem.*, 23, 577 (1986), and 2-chloromethyl-6-phenylpyridine by the method described in European Patent Publication No. 146,370.

Compounds of the invention which contain a basic nitrogen are capable of forming pharmacologically acceptable salts, including the salts of pharmacologically acceptable organic and inorganic acids such as hydrochloric, hydrobromic, sulfuric, nitric, phosphoric, methanesulfonic, benzenesulfonic, acetic, citric, fumaric, maleic, succinic and the like. The compounds which are carboxylic acids or have a hydroxamic function are capable of forming alkali metal and alkaline earth carboxylates and carboxylates of pharmacologically acceptable cations derived from ammonia or a basic amine. Examples of the latter include but are not limited to cations such as ammonium, mono-, di-, and trimethylammonium, mono-, di- and triethylammonium, mono-, di-, and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butyl-piperidinium, 2-methylpiperidinium, 1-ethyl-2-methylpiperidinium, mono-, di- and triethanolammonium, ethyl diethanolammonium, n-butylmonoethanolammonium, tris(hydroxymethyl)methylammonium, phenylmonoethanolammonium, and the like.

The compounds of the invention, by virtue of their ability to inhibit the activity of lipoxygenase enzyme and to antagonize mediators arising from this enzymatic pathway, are useful in the treatment of inflammatory conditions. Accordingly, the compounds are indicated in the treatment of such diseases as rheumatoid arthritis, osteoarthritis, tendonitis, bursitis and similar conditions involving inflammation. Moreover, by virtue of their ability to inhibit the activity of lipoxygenase enzyme and by their ability to antagonize the effect of LTC$_4$, LTD$_4$ and LTE$_4$ which are the constituents of SRS-A, they are useful for the inhibition of symptoms induced by these leukotrienes. Accordingly, the compounds are indicated in the prevention and treatment of those disease states in which LTC$_4$, LTD$_4$ and LTE$_4$ are causative factors, for example allergic rhinitis, allergic bronchial asthma and other leukotriene mediated naso-bronchial obstructive air-passageway conditions, as well as in other immediate hypersensitivity reactions, such as allergic conjunctivitis. The compounds are especially valuable in the prevention and treatment of allergic bronchial asthama.

When the compounds of the invention are employed in the treatment of allergic airways disorders and/or as antiinflammatory agents, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said composition both solid and liquid will be at least to impart the deisred activity thereto on oral administration. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The lipoxygenase inhibitory and leukotriene antagonist effects of the compounds of the invention may be demonstrated by standard pharmacological procedures, which are described more fully in the examples given hereinafter.

These procedures illustrate the ability of the compounds of the invention to inhibit the polymorphonuclear leukocyte synthesis of the lipoxygenase product 5,12-diHETE and the cyclooxygenase product TxB$_2$; the ability of the compounds to antagonize LTD$_4$-induced bronchospasm mediated by exogenously administered leukotrienes; measure the in vivo activity of the compounds as lipoxygenase inhibitors and leukotriene antagonists of endogenous mediators of bronchospasm and measure the in vivo antiinflammatory activity of the comounds in the rat carrageenan paw edema assay.

The following examples show the preparation and pharmacological testing of compounds within the invention.

EXAMPLE 1

1,1,1-Trifluoro-N-[3-[[2-(4-methoxyphenyl)-5-methyl-4-oxazolyl]methoxy]phenyl]methansulfonamide A. 2-(4-Methoxyphenyl)-5-methyl-4-[(3-nitrophenoxy)methyl]oxazole To a solution of 7.3 g (0.031 mol) of 4-(chloromethyl)-5-methyl-2-[4-(methoxyphenyl)]oxazole[1] and 4.3 g (0.031 mol) of 3-nitrophenol in 350 ml of acetone are added 2 g (0.037 mol) of cesium carbonate and 0.5 g potassium iodide and the slurry is heated to reflux for 20 hours. The mixture is filtered and the solution is concentrated in vacuo to obtain a residue. Recrystallization from acetone gives 6.15 g (59%) of crystals, m.p. 109°–111° C. The product is used without further purifications in subsequent reactions.

[1] Prepared according to the method of Goto et al., *Chem. Pharm. Bull.*, 19, 2050 (1971).

3-[[2-(4-Methoxyphenyl)-5-methyl-4-oxazolyl]methoxy]benzenamine

A solution of 6.0 g (0.18 mol) of 2-(4-methoxyphenyl)-5-methyl-4-[(3-nitrophenoxy)methyl]oxazole and 20.0 g (0.09 mol) of stannous chloride dihydrate in 150 ml of ethanol is heated to 70° C. for 20 hours. The solution is allowed to cool to room temperature and poured into 2 L of ice water. The mixture is made alkaline by the addition of solid sodium bicarbonate and extracted twice with 500 ml of ethyl acetate. The combined ethyl acetate solution is washed with 500 ml of brine, dried over anhydrous magnesium sulfate and concentrated in vacuo to obtain a residue. Recrystallization from ether/hexane gives 3.8 g (69%) of crystals, m.p. 132°–134° C. The product is used without further purification in subsequent reactions.

C. 1,1,1-Trifluoro-N-[3-[[2-(4-methoxyphenyl)-5-methyl-4-oxazolyl]methoxy]phenyl]methanesulfonamide A solution of 8.0 g (0.026 mol) of 3-[[2-(4-methoxyphenyl)-5-methyl-4-oxazolyl]methoxy]benzenamine and 3.1 g (0.031 mol) of triethylamine in 100 ml of methylene chloride is cooled to −78° C. A solution of 7.9 g (0.028 mol) of trifluoromethanesulfonic anhydride in 100 ml of methylene chloride is added from a dropping funnel and the mixture is allowed to warm to room temperature. The solution is concentrated in vacuo and the residue is dissolved in 400 ml of ethyl acetate/400 ml of water. The ethyl acetate layer is dried over anhydrous magnesium sulfate, and concentrated to obtain 10.9 g (95%) of crystals. Recrystallization from acetone/hexane gives 3.8 g (35%) of crystals, m.p. 201°–203° C.

Analysis for: $C_{19}H_{17}F_3N_2O_5S$; Calculated: C, 51.58; H, 3.87; N, 6.33; Found: C, 51.61; H, 3.91; N, 6.33.

EXAMPLE 2

1,1,1-Trifluoro-N-[3-[(5-methyl-2-phenyl-4-oxazolyl)methoxy]phenyl]methanesulfonamide

A. 5-Methyl-4-[(3-nitrophenoxy)methyl]-2-phenyloxazole

To a solution of 20.0 g (0.097 mol) of 4-chloromethyl-5-methyl-2-phenyloxazole[1] and 13.4 g (0.096 mol) of 3-nitrophenol in 500 ml of acetone are added 38.0 g (0.125 mol) of cesium carbonate and 1 g of potassium iodide, and the slurry is heated to reflux for 20 hours. The mixture is filtered, and concentrated in vacuo to obtain a residue. Recrystallization from acetone gives a first crop of 13.4 g (45%) of crystals, m.p. 106°-107° C., and a second crop of 6.6 g (22%) of crystals, m.p. 107°-108° C. The product is used without further purification in subsequent experiments.

[1] Prepared according to the method of Goto et al., *Chem. Pharm. Bull.*, 19, 2050 (1971).

B. 3-[(5-Methyl-2-phenyl-4-oxazolyl)methoxy]benzenamine

A solution of 20.0 g (0.065 mol) of 5-methyl-4-[(3-nitrophenoxy)methyl]-2-phenyloxazole and 73.0 g (0.325 mol) of stannous chloride dihydrate in 600 ml of ethanol is heated to 70° C. for 3 hours. The solution is allowed to cool to room temperature, and poured into 2 L of ice water. The mixture is made alkaline by the addition of solid sodium bicarbonate, and extracted twice with 500 ml of ethyl acetate. The combined ethyl acetate solution is concentrated in vacuo to obtain crystals. Recrystallization from acetone gives 8.5 g (47%) of crystals, m.p. 89°-90° C., MS (CI) 281 (M+H). The product is used without further purification in subsequent reactions.

C. 1,1,1-Trifluoro-N-[3-[(5-methyl-2-phenyl-4-oxazolyl)methoxy]phenyl]methansulfonamide

A solution of 8.5 g (0.03 mol) of 3-[(5-methyl-2-phenyl-4-oxazolyl)methoxy]benzenamine and 3.6 g (0.036 mol) of triethylamine in 75 ml of methylene chloride is cooled to −78° C. A solution of 9.2 g (0.033 mol) of trifluoromethanesulfonic anhydride in 80 ml of methylene chloride is added from a dropping funnel and the mixture is allowed to warm to room temperature. The solution is concentrated in vacuo and the residue is dissolved in 400 ml of ethyl acetate/400 ml of water. The ethyl acetate layer is dried over anhydrous magnesium sulfate, filtered through Celite and concentrated to obtain 10.0 g of crystals. Recrystallization from ether gives 6.6 g (52%) of crystals, m.p. 157°-159° C.

Analysis for: $C_{18}H_{15}F_3N_2O_4S$; Calculated: C, 52.38; H, 3.67; N, 6.79; Found: C, 52.36; H, 3.66; N, 6.67.

EXAMPLE 3

1,1,1-Trifluoro-N-[3-[(2-phenyl-4-thiazolyl)methoxy]phenyl]methanesulfonamide

A. 4-[(3-Nitrophenoxy)methyl]-2-phenylthiazole

To a solution of 6.5 g (0.046 mol) of 3-nitrophenol in 300 ml of acetone are added 11.6 g (0.047 mol) of 2-phenyl-4-chloromethylthiazole hydrochloride[2], 15 g (0.046 mol) of cesium carbonate, and 0.5 g of potassium iodide and the slurry is heated to reflux for 20 hours. The hot mixture is filtered and the filtrate is concentrated in vacuo to obtain 11.7 g (82%) crystalline residue. A part is recrystallized from ethyl acetate/pentane to give crystals, m.p. 112°-114° C.

Analysis for: $C_{16}H_{12}N_2O_3S$; Calculated: C, 61.52; H, 3.87; N, 8.97; Found: C, 61.01; H, 3.83; N, 8.87.

[2] Prepared according to the method of Marzoni, *J. Heterocyclic Chem.*, 23, 577 (1986).

B. 3-[(2-phenyl-4-thiazolyl)methoxy]benzenamine

A solution of 16.0 g (0.05 mol) of 4-[(3-nitrophenoxy)methyl-2-phenylthiazole and 56.5 g (0.25 mol) of stannous chloride dihydrate in 300 ml of absolute ethanol is heated to reflux for 20 hours. The mixture is poured into 2 L of water and made alkaline by the addition of solid sodium bicarbonate. The mixture is extracted twice with 1 L of ethyl acetate. The combined ethyl acetate layers are washed twice with dilute aqueous sodium chloride solution, dried over anhydrous magnesium sulfate, and concentrated in vacuo to obtain 12.0 g (85%) of an oil, which solidifies. The crystals, m.p. 75°-80° C., MS (CI) 283 (M+H), are used without further purification in subsequent reactions.

C. 1,1,1-Trifluoro-N-[3-[(2-phenyl-4-thiazolyl)methoxy]phenyl]methanesulfonamide

A solution of 6.0 g (0.0213 mol) of 3-[(2-phenyl-4-thiazolyl)methoxy]benzenamine and 2.6 g (0.025 mol) of triethylamine in 150 ml of methylene chloride is cooled to −78° C. A solution of 6.6 g (0.0234 mol) of trifluoromethanesulfonic anhydride in 50 ml of methylene chloride is added from a dropping funnel and the mixture is allowed to warm to room temperature. The solution is concentrated in vacuo and the residue is dissolved in 300 ml of ethyl acetate/300 ml of water. The layers are separated and the ethyl acetate solution is washed with brine, dried over anhydrous magnesium sulfate, and concentrated to an oil (11 g). The oil is chromatographed with ethyl acetate/hexane as eluent. Fraction 2 is concentrated to an oil (5.4 g), which is triturated with ethyl acetate/hexane, 9/1 (v/v) to obtain 4.0 g (45%) of crystals, m.p. 113°-115° C.

Analysis for: $C_{17}H_{13}F_3N_2O_3S_2$; Calculated: C, 49.27; H, 3.16; N, 6.76; Found: C, 49.28; H, 3.13; N, 6.76.

EXAMPLE 4

1,1,1-Trifluoro-N-[2-[(2-phenyl-4-thiazolyl)methoxy]phenyl]methanesulfonamide

A. 4-[(2-nitrophenoxy)methyl]-2-phenylthiazole

To a solution of 10.7 g (0.08 mol) of 2-nitrophenol in 500 ml of acetone are added 19.0 g (0.08 mol) of 4-chloromethyl-2-phenylthiazole hydrochloride, 26.3 g (0.08 mol) of cesium carbonate, and 0.5 g of potassium iodide, and the slurry is heated to reflux for 20 hours. The mixture is filtered, and the filtrate is concentrated in vacuo to obtain a crystalline residue. Recrystallization from ethanol gives 16.7 g (67%) of crystals, m.p. 95° C.

Analysis for: $C_{16}H_{12}N_2O_3S$; Calculated: C, 61.52; H, 3.87; N, 8.97; Found: C, 61.42; H, 4.06; N, 8.88.

B. 2-[(2-phenyl-4-thiazolyl)methoxy]benzenamine

A solution of 16.0 g (0.05 mol) of 4-[(2-nitrophenoxy)methyl-2-phenylthiazole and 56.5 g (0.25 mol) of stannous chloride dihydrate in 300 ml of ethanol is refluxed for 20 hours. The mixture is poured into 2 L of ice water and made alkaline by the addition of solid sodium bicarbonate. The mixture is extracted twice with 1 L of ethyl acetate. The combined ethyl acetate layers are washed twice with dilute brine, dried over anhydrous magnesium sulfate, and concentrated in vacuo to obtain 15.3 g of an oil. 8.5 Grams of the oil are subjected to high pressure liquid chromatography (ethyl acetate/hexane as eluent). Fractions 18-21 are combined and concentrated to obtain 5.4 g (38%) of crystals, m.p. 60°-62° C.

Analysis for: $C_{16}H_{14}N_2OS$; Calculated: C, 68.06; H, 5.00; N, 9.92; Found: C, 68.06; H, 4.99; N, 9.92.

C. 1,1,1-Trifluoro-N-[2-[(2-phenyl-4-thiazolyl)methoxy]phenyl]methanesulfonamide A solution of 6.3 g (0.022 mol) of 2-[(2-phenyl-4-thiazolyl)methoxy]benzenamine and 3.0 g (0.03 mol) of triethylamine in 150 ml of methylene chloride is cooled to −70° C. A solution of 6.6 g (0.0234 mol) of trifluoromethanesulfonic anhydride in 50 ml of methylene chloride is added from a dropping funnel, and the mixture is allowed to warm to room temperature. The solution is concentrated in vacuo and the residue is dissolved in 300 ml of ethyl acetate/300 ml of dilute hydrochloric acid. The layers are separated and the aqueous phase is extracted with 300 ml of ethyl acetate. The combined ethyl acetate solution is twice washed with dilute brine, dried over anhydrous magnesium sulfate and concentrated to an oil, which is subjected to high pressure liquid chromatography (ethyl acetate/hexane as eluent). Fractions 7-10 are combined and concentrated to obtain 5.0 g of crystals, m.p. 122°-125° C. The crystals are triturated with ethyl acetate to obtain 2.6 g (29%) of crystals, m.p. 123°-125° C.

Analysis for: $C_{17}H_{13}F_3N_2O_3S$ Calculated: C, 49.27; H, 3.16; N, 6.76 Found: C, 49.32; H, 3.23; N, 6.70.

EXAMPLE 5

5-[[3-(2-Phenyl-4-thiazolylmethoxy)phenyl]methyl]-1H-tetrazole

A. 3-(2-Phenyl-4-thiazolylmethoxy)benzenacetonitrile

To a solution of 14.0 g (0.105 mol) of 3-hydroxyphenylacetonitrile in 500 ml of acetone were added 25.9 g (0.105 mol) of 4-chloromethyl-2-phenylthiazole hydrochloride and 34.2 g (0.105 mol) of cesium carbonate and 1 g of potassium iodide and the slurry is heated to reflux for 20 hours. The mixture is filtered and the solution is concentrated in vacuo to obtain crystals. Recrystallization from ethyl acetate gives 14.0 g (43%) crystals, m.p. 108°-110° C. The product is used without further purification in subsequent reactions.

B. 5-[[3-(2-Phenyl-4-thiazolylmethoxy)phenyl]methyl]-1H-tetrazole

To a solution of 9.0 g (0.03 mol) of 3-(2-phenyl-4-thiazolylmethoxy)benzenacetonitrile in 200 ml of dimethylformamide are added 9.5 g (0.15 mol) of sodium azide and 7.9 g (0.15 mol) of ammonium chloride, and the slurry is heated to 135° C. for 72 hours. The mixture is allowed to cool to room temperature, diluted with 200 ml of water, and extracted four times with 200 ml of ethyl acetate. The combined ethyl acetate solution is washed with brine, dried over anhydrous magnesium sulfate, and concentrated in vacuo to obtain an oil, which is subjected to high pressure liquid chromatography (ethyl acetate/hexane as eluent). Fraction 2 is concentrated to obtain 3.0 g (29%) of crystals, m.p. 160°-161° C.

Analysis for: $C_{18}H_{15}N_5OS$ Calculated: C, 61.87; H, 4.32; N, 20.05 Found: C, 61.62; H, 4.50; N, 19.98.

EXAMPLE 6

N,N-Diethyl-N'-[2-hydroxy-2-[3-(2-phenyl-4-thiazolylmethoxy)phenyl]ethyl]-N-methylurea To a solution of 14.0 g (0.053 mol) of N,N-diethyl-N'-[2-hydroxy-2-(3-hydroxyphenyl)ethyl]-N'-methylurea in 200 ml of acetone are added 13.0 g (0.053 mol) of 4-chloromethyl-2-phenylthiazole hydrochloride, 13 g (0.053 mol) of cesium carbonate and 1 g of potassium iodide, and the slurry is refluxed for 20 hours. The mixture is poured into 500 ml of water/500 ml of ethyl acetate and the layers are separated. The aqueous phase is twice extracted with 300 ml of ethyl acetate, and the combined ethyl acetate solution is twice washed with brine, dried over anhydrous magnesium sulfate and concentrated in vacuo to obtain an oil, which is subjected to high pressure liquid chromatography (ethyl acetate/hexane as eluent). Fractions 4-12 are combined and concentrated to give an oil, which is rechromatographed. Fractions 9-10 are combined and concentrated in vacuo to obtain 4.0 g (17%) of a viscous oil.

Analysis for: $C_{24}H_{29}N_3O_3S$ Calculated: C, 65.57; H, 6.65; N, 9.56 Found: C, 65.20; H, 6.76; N, 9.22.

EXAMPLE 7

1,1,1-Trifluoro-N-[3-[(2-phenyl-6-pyridinyl)methoxy]phenyl]methanesulfonamide

A. 6-[(3-Nitrophenoxy)methyl]-2-phenylpyridine

To a stirred solution of 4.2 g (0.03 mol) of 3-nitrophenol in 150 ml of acetone is added 7.5 g (0.05 mol) of 2-chloromethyl-6-phenylpyridine hydrochloride[3], 10 g (0.03 mol) of cesium carbonate and 0.5 g of potassium iodide, and the slurry is heated to reflux for 20 hours. The hot mixture is filtered, and the filtrate is concentrated in vacuo to obtain an oil (9.3 g). The crude product is recrystallized from ethyl acetate/pentane to give a first crop (4.5 g, 49%) of crystals, m.p. 77°-80° C. and a second crop (1.7 g, 19%) of crystals, m.p. 77°-81° C.

Analysis for: $C_{18}H_{14}N_2O_3$ Calculated: C, 70.58; H, 4.61; N, 9.15 Found: C, 70.56; H, 4.51; N, 9.19.

[3] Prepared according to the method described in European Patent Publication No. 146,370.

B. 3-[(2-Phenyl-6-pyridinyl)methoxy]benzenamine

A suspension of 6.2 g (0.02 mol) of 6-[(3-nitrophenoxy)methyl]-2-phenylpyridine in a solution of 50.0 g (0.18 mol) of ferrous sulfate heptahydrate and 0.3 ml of concentrated hydrochloric acid in 100 ml of water is heated on a steambath to 90° C. Concentrated ammonium hydroxide is added in 3 increments of 10 ml over a period of 10 minutes. Heating is discontinued and the reaction mixture is allowed to cool over a period of 45 minutes while vigorously stirring. The reaction mixture is diluted with 300 ml of water/300 ml of ethyl acetate and filtered through Celite. The filter cake is extracted once with 300 ml of ethyl acetate, and the combined ethyl acetate solution is concentrated in vacuo to obtain an oil (4.8 g). The oil is chromatographed with ethyl acetate/hexane as eluent. Fractions 8-11 are combined and concentrated to obtain 2.0 g (37%) of an oil, MS (CI) 277 (M+H). The product is used without further purification in subsequent reactions.

C. 1,1,1-Trifluoro-N-[3-[(2-phenyl-6-pyridinyl)methoxy]phenyl]methanesulfonamide A solution of 2.0 g (0.00725 mol) of 3-[(2-phenyl-6-pyridinyl)methoxy]benzenamine and 2.0 g (0.02 mol) of triethylamine in 150 ml of methylene chloride is cooled to −70° C. A solution of 2.1 g (0.00745 mol) of trifluoromethanesulfonic anhydride in 50 ml of methylene chloride is added from a dropping funnel and the mixture is allowed to warm to room temperature. The solution is concentrated in vacuo, and the residue is dissolved in 250 ml of ethyl acetate/250 ml of acidic, dilute aqueous sodium chloride solution. The layers are separated and the aqueous phase is extracted with 250 ml of ethyl acetate. The combined ethyl acetate solution is washed with brine, dried over anhydrous magnesium sulfate and concentrated to obtain an oil, MS (CI) 409 (M+H), 541 (M+H for disubstituted product). The oil is dissolved in 25 ml of methanol and stirred with 25 ml of Claisen's Alkali for 2 hours at room temperature. The reaction mixture is diluted with water, acidified, and extracted twice with ethyl acetate. The combined ethyl acetate solution is washed with brine, dried over anhydrous magnesium sulfate to obtain an oil (0.5 g), MS (CI) 409 (M+H), which crystallizes. The crystals are triturated with ethyl acetate/pentane to obtain 0.17 g (2.1%) crystals, m.p. 115°–117° C.

Analysis for: $C_{19}H_{15}F_3N_2O_3S$ Calculated: C, 55.87; H, 3.70; N, 6.86 Found: C, 55.79; H, 3.66; N, 6.76.

EXAMPLE 8

N-[(4-Methylphenyl)sulfonyl]-3-[(2-phenyl-4-thiazolyl)methoxy]benzamide

A. 3-[(2-Phenyl-4-thiazolyl)methoxy]benzoic acid

A slurry of 10.5 g (0.05 mol) of 2-phenyl-4-chloromethylthiazole, 7.6 g (0.05 mol) of methyl-3-hydroxybenzoate, 16.2 g (0.05 mol) of cesium carbonate, and 0.1 g of potassium iodide in 100 ml of acetone is refluxed for 16 hours. The mixture is filtered and the solution is concentrated in vacuo to obtain 15.5 g of oil. To 2.0 g of this oil is added 60 ml 1N NaOH and 40 ml tetrahydrofuran and the mixture refluxed 2 hours. The mixture is concentrated in vacuo to an aqueous solution. The aqueous solution is acidified to pH 6 and filtered to get 5.5 g solids, m.p. 155°–157° C.

Analysis for: $C_{17}H_{13}NO_3S$ Calculated: C, 65.57; H, 4.21; N, 4.50 Found: C, 65.15; H, 4.24; N, 4.10.

B. N-[(4-Methylphenyl)sulfonyl]-3-[(2-phenyl-4-thiazolyl)methoxy]benzamide

To a solution of 5.48 g (0.0176 mol) of 3-[(2-phenyl-4-thiazolyl)methoxy]benzoic acid in 100 ml of toluene are added 3.24 g (0.0200 mol) of 1,1'-carbonyldiimidazole and the solution is stirred for 1 hour. To this solution, 3.01 g (0.0176 mol) p-toluenesulfonamide are added and the solution is refluxed for 16 hours. After cooling, the bottom layer is isolated and concentrated in vacuo to obtain a clear oil. The clear oil is dissolved in methylene chloride and is washed twice with pH 4 buffer solution, twice with water and is concentrated in vacuo to obtain a residue. Recrystallization from toluene/ethyl acetate gives 1.5 g (18%) of crystals, m.p. 170°–172° C.

Analysis for: $C_{24}H_{20}N_2O_4S_2$ Calculated: C, 62.05; H, 4.34; N, 6.03 Found: C, 62.20; H, 4.50; N, 5.87.

EXAMPLE 9

Following the procedure of Example 3 and using the appropriate 2-substituted-4-chloromethylthiazole hydrochloride starting material, the following compounds are prepared:

A. 1,1,1-Trifluoro-N-[3-[[2-(4-chlorophenyl)-4-thiazolyl]methoxy]phenyl]methanesulfonamide, m.p. 147°–149° C.

Analysis for: $C_{17}H_{12}ClF_3N_2O_3S_2$ Calculated: C, 45.49; H, 2.70; N, 6.24 Found: C, 45.58; H, 2.91; N, 6.01.

B. 1,1,1-Trifluoro-N-[3-[[2-(4-fluorophenyl)-4-thiazolyl]methoxy]phenyl]methanesulfonamide, m.p. 134°–136° C.

Analysis for: $C_{17}H_{12}F_4N_2O_3S_2$ Calculated: C, 47.22; H, 2.80; N, 6.48 Found: C, 47.24; H, 2.86; N, 6.38.

C. 1,1,1-Trifluoro-N-[3-[[2-(2-fluorophenyl)-4-thiazolyl]methoxy]phenyl]methanesulfonamide, m.p. 152°–154° C.

Analysis for: $C_{17}H_{12}F_4N_2O_3S_2$ Calculated: C, 47.22; H, 2.80; N, 6.48 Found: C, 47.46; H, 3.12; N, 6.55.

D. 1,1,1-Trifluoro-N-[3-[[2-(2,6-difluorophenyl)-4-thiazolyl]methoxy]phenyl]methanesulfonamide, m.p. 169°–172° C.

Analysis for: $C_{17}H_{11}N_2F_5O_3S_2$ Calculated: C, 45.33; H, 2.46; N, 6.22 Found: C, 45.55; H, 2.65; N, 6.18.

E. 1,1,1-Trifluoro-N-[3-[[2-(4-trifluoromethylphenyl)-4-thiazolyl]methoxy]phenyl]methanesulfonamide, m.p. 144°–146° C.

Analysis for: $C_{18}H_{12}F_6N_2O_3S_2$ Calculated: C, 44.81; H, 2.51; N, 5.81 Found: C, 44.89; H, 2.68; N, 5.63.

F. 1,1,1-Trifluoro-N-[3-[[2-(3-trifluoromethylphenyl)-4-thiazolyl]methoxy]phenyl]methanesulfonamide, m.p. 138°–142° C.

Analysis for: $C_{18}H_{12}F_6N_2O_3S_2$ Calculated: C, 44.81; H, 2.51; N, 5.81 Found: C, 44.77; H, 2.89; N, 5.84.

G. 1,1,1-Trifluoro-N-[3-[[2-(2-trifluoromethylphenyl)-4-thiazolyl]methoxy]phenyl]methanesulfonamide, m.p. 109°–111° C.

Analysis for: $C_{18}H_{12}F_6N_2O_3S_2$ Calculated: C, 44.81; H, 2.51; N, 5.81 Found: C, 44.89; H, 2.76; N, 5.81.

H. 1,1,1-Trifluoro-N-[3-[[2-(4-methoxyphenyl)-4-thiazolyl]methoxy]phenyl]methanesulfonamide, m.p. 154°–157° C.

Analysis for: $C_{18}H_{15}F_3N_2O_4S_2$ Calculated: C, 48.64; H, 3.40; N, 6.30 Found: C, 49.00; H, 3.29; N, 6.24.

I. 1,1,1-Trifluoro-N-[3-[[2-(benzyl)-4-thiazolyl]methoxy]phenyl]methanesulfonamide, m.p. 146°–149° C.

Analysis for: $C_{18}H_{15}F_3N_2O_3S_2$ Calculated: C, 50.46; H, 3.53; N, 6.54 Found: C, 50.31; H, 3.74; N, 6.22.

EXAMPLE 10

3-[[2-(2-Fluorophenyl)-4-thiazolyl]methoxy]benzoic acid hydrazide

A. 3-[[2-(2-Fluoromethyl)-4-thiazolyl]methoxy]benzoic acid methyl ester

A stirred mixture of 0.23 g (0.001 mol) of 4-[[3-(chloromethyl)phenoxy]methyl]-2-(2-fluorophenyl)-thiazole, 0.15 g (0.001 mol) of methyl-3-hydroxybenzoate and 0.32 g (0.001 mol) of cesium carbonate in 20 ml of acetone is heated under reflux for 3 hours. The mixture is filtered and the filtrate is evaporated in a rotary evaporator. The residue is recrystallized from heptane to give 0.09 g of product, m.p. 83°–86° C.

Analysis for: $C_{18}H_{14}FNO_3S$ Calculated: C, 62.96; H, 4.11; N, 4.08 Found: C, 63.40; H, 4.33; N, 4.33.

B. 3-[[2-(2-Fluorophenyl)-4-thiazolyl]methoxy]benzoic acid hydrazide

A stirred mixture of 5.0 g of 3-[[2-(2-fluoromethyl)-4-thiazolyl]methoxy]benzoic acid methyl ester in 70 ml of methanol containing 5 ml of hydrazine hydrate is heated under reflux for 24 hours. The mixture is cooled and the insoluble material is collected. The filter cake is recrystallized from acetonitrile to afford 3.5 g of title product, m.p. 143°–145° C.

Analysis for: $C_{17}H_{14}FN_3O_2S$ Calculated: C, 59.46; H, 4.11; N, 12.24 Found: C, 59.52; H, 4.29; N, 12.44.

EXAMPLE 11

5-[3-[[2-(2-Fluorophenyl)-4-thiazolyl]methoxy]phenyl]-1,3,4-oxadiazol-2(3H)-one

A stirred mixture of 3.4 g (0.01 mol) of 3-[[2-fluorophenyl)-4-thiazolyl]methoxy]benzoic acid hydrazide prepared according to Example 10 and 1.6 g (0.01 mol) of 1,1'-carbonyldiimidazole in 50 ml of dichloromethane is heated under reflux for 3 hours. The mixture is evaporated in a rotary evaporator and the residue is recrystallized from ethanol to provide 2.5 g of title product, m.p. 198°–202° C.

Analysis for: $C_{18}H_{12}FN_3O_3S$ Calculated: C, 58.53; H, 3.28; N, 11.38 Found: C, 58.79; H, 3.53; N, 11.47.

EXAMPLE 12

The compounds 5- and 12-hydroxyeicosatetraenoic acid (5-HETE and 12-HETE) and 5,12-dihydroxyeicosatetraenoic acid (5,12-diHETE) are early arachidonic acid oxidation products in the lipoxygenase cascade, which have been shown to mediate several aspects of inflammatory and allergic response. This is especially true with respect to 5,12-diHETE, which is also denoted as $LTB_4$ [see Ford-Hitchinson, *J. Roy. Soc. Med.*, 74, 831 (1981)]. The assay of this Example measures the ability of the compounds of the invention to inhibit the synthesis of 5,12-diHETE by rat glycogenelicited polymorphonuclear leukocytes.

The assay is carried out as follows:

Peritoneal PMN are obtained from female Wistar rats (150–250 g) that received an i.p. injection of 6% glycogen (10 ml). After 24 hours, rats are killed by $CO_2$ asphyxiation and peritoneal cells are harvested by peritoneal lavage using $Ca^{++}$ and $Mg^{++}$ free Hanks' balanced salt solution (HBSS). The peritoneal exudate is centrifuged at 400 g for 10 minutes. After centrifugation, the lavaged fluid is removed and the cell pellet is resuspended in HBSS containing $Ca^{++}$ and $Mg^{++}$ and 10 mM L-cysteine at a concentration of $2 \times 10^7$ cells/ml. To 1 ml portions of cell suspension, test drugs or vehicle are added and incubated at 37° C. for 10 minutes. Following this preincubation, the calcium ionophore (10 μM), A23187, is added together with 0.5 μCi [$^{14}$C] arachidonic acid and further incubated for 10 minutes. The reaction is stopped by the addition of ice cold water (3 ml) and acidification to pH 3.5. Lipoxygenase products are then extracted twice into diethyl ether. The pooled ether extracts are evaporated to dryness under nitrogen and the residue is redissolved in a small volume of methanol and spotted on aluminum backed pre-coated thin layer chromatographic plates. The samples are then co-chromatographed with authentic reference 5,12-diHETE in the solvent system-hexane: ether: acetic acid (50:50:3). After chromatography, the areas associated with 5,12-diHETE standard are identified by autoradiography, cut out and quantitated by liquid scintillation.

Results are expressed as the 50% Inhibitory concentration, or as percent inhibition at a given.

Testing compounds of the invention in this assay gives the following results:

TABLE I

| Compound of Example Number | 50% Inhibitory Concentration $(IC_{50})\mu m$ |
|---|---|
| 3 | 3.2 |
| 8 | 55% at 10 μM |
| 9A | 5.2 |
| 9B | 64% at 10 μM |

The results show that compounds of this invention have significant activity in inhibiting the synthesis of the arachidonic acid lipoxygenase oxidation product 5,12-diHETE.

EXAMPLE 13

The procedure of Example 12 is also employed for the determination of the ability of the compounds of the invention to inhibit the synthesis of the arachidonic acid cyclooxygenase oxidation product $TxB_2$.

In this assay, the procedure of Example 12 is carried out as described. However, in order to determine cyclooxygenase activity, the samples are cochromatographed with authentic reference $TxB_2$ in the solvent system ethyl acetate: formic acid (80:1) and the upper phase of ethyl acetate: isoctane: acetic acid: water (110:50:20:100). After chromatography, the areas associated with $TxB_2$ standard are identified by autoradiography, cut out and quantitated by liquid scintillation techniques.

The results are calculated as in Example 12 and presented below:

TABLE II

| Compound of Example Number | 50% Inhibitory Concentration $(IC_{50})\mu M$ |
|---|---|
| 3 | 1.7 |
| 8 | 44% at 10 μM |
| 9A | 7.1 |
| 9B | 32% at 10 μM |

The results show that the compounds tested have significant activity in inhibiting the synthesis of the arachidonic acid cyclooxygenase oxidation product $TxB_2$.

EXAMPLE 14

The assay of this Example measures the in vivo ability of the compounds of the invention to inhibit the bronchospasm induced in guinea pigs by the exogenously administered leukotrienes $C_4$ and/or $D_4$. This assay is essentially a measure of the SRS-A antagonist properties of the compounds tested.

This assay is carried out as follows:

Male Hartley strain guinea pigs (350–600 g) are anesthetized with pentobarbital sodium (50 mg/kg, i.p.). The jugular vein is cannulated for injection of drugs and the carotid artery for monitoring blood pressure. The trachea is cannulated for artificial ventilation by a miniature Starling pump and for indirect measurement of respiratory volume changes as described infra. Additional pentobarbital sodium (15 mg/kg, i.v.) is administered to arrest spontaneous respiration. Submaximal bronchoconstrictor responses are established in control animals by varying the dose-levels of leukotriene. Intravenous dose-levels for $LTC_4$ range from 1 to 2 μg/kg and for $LTD_4$ the range is from 0.3 to 1 μg/kg. The aerosol bronchoprovocation dose for $LTC_4$ is generated from 1.6 μM solution and for $LTD_4$ from a 2.0 μM solution.

Test drugs are administered either intravenously, intragastrically, by aerosol or orally at 1 or 10 minutes before induction of bronchospasm by administration of either $LTC_4$ or $LTD_4$ at the predetermined dose-levels. Aerosols of soluble drugs or leukotrienes are produced in-line for 10 seconds only by actuation of an ultrasonic nebulizer (Monaghan). Aerosolized drug dosage is expressed in terms of solution concentration and by a fixed aerosol exposure time (approximately 10 seconds). Control animals receive saline in place of drug.

Respiratory volume changes are determined by a calibrated piston whose travel is recorded, via a linear transducer, on a Beckman Dynograph recorder. Maximal bronchoconstrictor volume is determined by clamping off the trachea at the end of the experiment. Overflow volumes at 1, 3 and 5 minutes are obtained from the recorded charts.

Area under the volume overflow curve (AUC) is estimated, using the overflow values at 1, 3 and 5 minutes, and expressed as a percentage of the maximal overflow AUC (equation 1):

$$\%\max AUC = \frac{3(1 \min) + 4(3 \min) + 2(5 \min)}{10(\max)} \times 100 \quad (1)$$

Drug effects are reported as percent inhibition of % max AUC values obtained from appropriate control animals (equation 2):

$$\% \text{ inhibition} = \frac{\% \max AUC \text{ control} - \% \max AUC \text{ treated}}{\% \max AUC \text{ control}} \times 100 \quad (2)$$

Student's t-test for unpaired data is used to determine statistical significance ($p<0.05$). $ED_{50}$ values can also be determined by inverse prediction from linear regression lines through points between 10 and 90% inhibition.

The results for a compound of the invention are as follows:

TABLE III

| Compound administered at 10 minutes before induction of bronchospasm | | | |
|---|---|---|---|
| Compound of Example Number | Dose (mg/kg) | % Inhibition | $ED_{50}$ (mg/kg) |
| 1 | 25* | 24 | |
| 2 | 25* | 56 | |
| 3 | | | 2.4*  3.0** |
| 4 | 25* | 10 | |
| 5 | 25* | 69 | |
| 6 | 25* | 47 | |
| 7 | 25* | 68 | |
| 8 | 25* | 62 | |
| 9A | 25* | 54 | |
| 9B | 25* | 100 | |
| | 10** | 92 | |
| 9C | 25* | 73 | |
| | 10** | 89 | |
| 9D | 25* | 72 | |
| 9F | 25* | 50 | |
| 9I | 25* | 94 | |
| | 25** | 47 | |

*intraduodenally administered
**intragastrically administered

The results show that compounds of the invention have in vivo activity against $LTD_4$ induced bronchoconstriction.

EXAMPLE 15

The assay of this Example measures the in vivo ability of the compounds of the invention to inhibit the bronchospasm induced in guinea pigs by endogenous mediators of the bronchoconstriction.

The assay is carried out as follows:

Male Hartley strain guinea pigs weighing 250–350 g are sensitized to chicken ovalbumin (OA) (10 mg i.p.) on days 1 and 3 and used starting on day 26. The animals are anesthetized with pentobarbital sodium (50 mg/kg, i.p.), bilateral vagotomy is performed, and the jugular vein is cannulated for injection of drugs and the carotid artery for monitoring blood pressure. The trachea is cannulated for artificial ventilation by miniature Starling pump and for indirect measurement of respiratory volume changes as described, infra. Succinylcholine (2 mg/kg, i.v.) is administered to arrest spontaneous respiration. A cyclooxygenase inhibitor, indomethacin (10 mg/kg in tris buffer, i.v. at 9 min.) is administered to shunt arachidonic metabolism to lipoxygenase pathways. One minute later, chlorpheniramine (1.0 mg/kg in saline, i.v.) is given to attenuate the histaminic component of anaphylactic bronchoconstriction. Test drugs (dissolved in propylene glycol, polyethylene glycol or saline) are administered either intraduodenally, intragastrically or by aerosol at 2 or 10 minutes before antigen challenge. Anaphylactic bronchoconstriction is induced by administration by breaths of aerosolized OA (1%) or by intravenous administration of 0.1–0.3 mg/kg OA in saline. Control animals receive solvent (2 ml/kg i.d. or appropriate aerosol) in place of drug.

Respiratory volume changes are determined by a calibrated piston whose travel is recorded, via a linear transducer, on a Beckman Dynograph recorder. Maximal bronchoconstrictor volume is determined by clamping off the trachea at the end of the experiment. Overflow volumes at minutes 1, 3 and 5 are obtained from the recorded charts.

Area under the volume overflow curve (AUC) is estimated, using the overflow values at 1, 3 and 5 minutes, and expressed as a percentage of the maximal overflow AUC (equation 1):

$$\%\max AUC = \frac{3(1 \min) + 4(3 \min) + 2(5 \min)}{10(\max)} \times 100 \quad (1)$$

Drug effects are reported as percent inhibition of % max AUC values obtained from appropriate control animals (equation 2):

$$\% \text{ inhibition} = \frac{\% \max AUC \text{ control} - \% \max AUC \text{ treated}}{\% \max AUC \text{ control}} \times 100 \quad (2)$$

Students t-test for unpaired data is used to determine statistical significance. Dose response curves are generated and $ED_{50}$ doses are interpolated from the regression lines.

The results for a compound of the invention in this assay, using $LTD_4$ for induction of bronchospasm, are given below:

TABLE IV

| Compound administered at 10 minutes before intravenously administered ovalbumin challenge | | |
|---|---|---|
| Compound of Example Number | Dose mg/kg | % Inhibition |
| 3 | 10* | 81 |
|   | 25** | 10 |
| 9B | 10** | 22 |
| 9C | 10** | 60 |

*intraduodenally administered
**intragastrically administered

The results show that the compounds tested have moderate to significant in vivo activity in inhibiting ovalbumin induced bronchospasm mediated by endogenous products of the lipoxygenase oxidation of arachidonic acid.

EXAMPLE 16

The compounds of the invention are tested in the rat carrageenan paw edema assay to determine their ability to inhibit the acute inflammatory response.

This assay is carried out as follows:

140–180 gm male Sprague-Dawley rats, in groups of 6 animals, are injected subcutaneously in the right paw with 0.1 ml of 1% carrageenan at zero time. Mercury plethysmographic readings (ml) of the paw are made at zero time and 3 hours later. Test compounds are suspended or dissolved in 0.5% methylcellulose and given perorally 1 hour prior to carrageenan administration.

The increase in paw volume (edema in ml.) produced by the carrageenan is measured. Paw edema is calculated (3 hour volume minus zero time volume), and percent inhibition of edema is determined. Unpaired Student's t-test is used to determine statistical significance.

The activity of standard drugs in this assay is as follows:

| Drug | Oral $ED_{50}$ (95% C.L.)mg/kg |
|---|---|
| Indomethacin | 3.7(0.6, 23.8) |
| Aspirin | 145.4(33.1, 645.6) |
| Phenylbutazone | 26.2(2.3, 291.0) |

When tested in this assay, the compounds of the invention gave the following results:

| Compound of Example No. | % Inhibition at 50 mg/kg (peroral) |
|---|---|
| 1 | 34 |
| 2 | 18 |
| 3 | 51 |
| 6 | 57 |
| 8 | 51 |
| 9A | 60 |
| 9B | 55 |
| 9C | 53 |
| 9D | 37 |
| 9E | 66 |
| 9F | 23 |
| 9I | 22 |

The results show that the compounds tested have activity in the rat carrageenan paw edema assay, evidencing an effect on the acute inflammatory response.

What is claimed is:

1. A compound having the formula wherein
Z is $-(CH_2)_nO-$, $-(CH_2)_nS-$, $$-(CH_2)_n\overset{O}{\overset{\|}{S}}-$$

or $-(CH_2)_nSO_2-$;

$$-(CH_2)_n\overset{R^4}{\overset{|}{N}}-SO_2R^5 \text{ or } -(CH_2)_n-\overset{O}{\overset{\|}{C}}-\overset{}{\underset{R^4}{N}}SO_2R^5$$

n is 0–5;
$R^2$ is, independently, hydrogen, loweralkyl, loweralkoxy, trifluoromethyl or halo;

$R^3$ is $-(CH_2)_mW-$〔phenyl-$R^2$〕 or 〔phenyl-$R^2$〕;

W represents a bond or $-O-$, $-S-$ or $-\overset{}{\underset{R^4}{N}}-$;

m is 1–15;
$R^4$ is hydrogen or loweralkyl;
$R^5$ is lower alkyl, monofluoroloweralkyl, difluoroloweralkyl, polyfluoroloweralkyl, perfluoroloweralkyl or 〔phenyl-$R^2$〕;

or a pharmaceutically acceptable salt thereof.

2. The compound of claim 1, which is 1,1,1-trifluoro-N-[3-[(2-phenyl-6-pyridinyl)methoxy]phenyl]methanesulfonamide.

* * * * *